(12) United States Patent
Smith et al.

(10) Patent No.: US 6,838,163 B2
(45) Date of Patent: Jan. 4, 2005

(54) COMPOSITE FACER FOR WALLBOARDS

(75) Inventors: Robert M. Smith, Duncan, SC (US); George C. McLarty, III, Greenville, SC (US); Andrew D. Child, Moore, SC (US); Samuel E. Graham, LaGrange, GA (US); W. Randolph Hursey, LaGrange, GA (US)

(73) Assignee: Milliken & Company, Spartanburg, SC (US)

( * ) Notice: Subject to any disclaimer, the term of this patent is extended or adjusted under 35 U.S.C. 154(b) by 192 days.

(21) Appl. No.: 09/833,358

(22) Filed: Apr. 12, 2001

(65) Prior Publication Data

US 2002/0151240 A1 Oct. 17, 2002

(51) Int. Cl.$^7$ .............................................. B32B 13/02
(52) U.S. Cl. ............................... 428/294.7; 428/312.4; 442/374; 442/375; 442/381; 442/398
(58) Field of Search ........................ 428/312.4, 294.7, 428/703; 52/782.1; 442/374, 375, 381, 398, 42, 383, 384

(56) References Cited

U.S. PATENT DOCUMENTS

| | | | |
|---|---|---|---|
| 3,944,698 A | 3/1976 | Dierks et al. | 428/219 |
| 3,993,822 A | 11/1976 | Knauf et al. | 428/213 |
| 4,020,237 A | 4/1977 | Von Hazmburg | 428/535 |
| 4,378,405 A | 3/1983 | Pilgrim | 428/322.7 |
| 4,504,533 A | 3/1985 | Altenhöfer et al. | 428/70 |
| 4,544,424 A | 10/1985 | Take et al. | 156/39 |
| 4,916,004 A | 4/1990 | Ensminger et al. | 428/192 |
| 5,030,502 A | 7/1991 | Teare | 428/193 |
| 5,220,762 A | 6/1993 | Lehnert et al. | 52/408 |
| 5,225,237 A | 7/1993 | Magnani | 442/57 |
| 6,054,205 A | 4/2000 | Newman et al. | 428/221 |
| 6,176,920 B1 | 1/2001 | Murphy et al. | 106/711 |
| 2002/0019181 A1 * | 2/2002 | Cooper et al. | 442/43 |

FOREIGN PATENT DOCUMENTS

| | | |
|---|---|---|
| DE | 2854228 | 6/1980 |
| DE | 3406449 | 8/1985 |
| FR | 2 323 504 | 9/1975 |
| JP | 53-146724 | 12/1978 |
| JP | 55-146736 | 11/1980 |
| JP | 4069301 | 3/1992 |

* cited by examiner

Primary Examiner—Terrel Morris
Assistant Examiner—Andrew T. Piziali
(74) Attorney, Agent, or Firm—Terry T. Moyer; Charlotte C. Wilson

(57) ABSTRACT

A composite facer material for use with cementitious wallboards, where the composite facer is embedded in a top and bottom face thereof. The composite facer material, in a most preferred embodiment, comprises two layers. The first layer is preferably a carded polyester nonwoven mat, which is bonded to a second layer comprising preferably a tri-directional laid scrim fabric reinforcement layer made of continuous glass fibers. The two layers are preferably bonded together using an acrylic adhesive, which offers superior adhesion between the layers as well as superior adhesion between the composite facing material and the cementitious core.

34 Claims, 1 Drawing Sheet

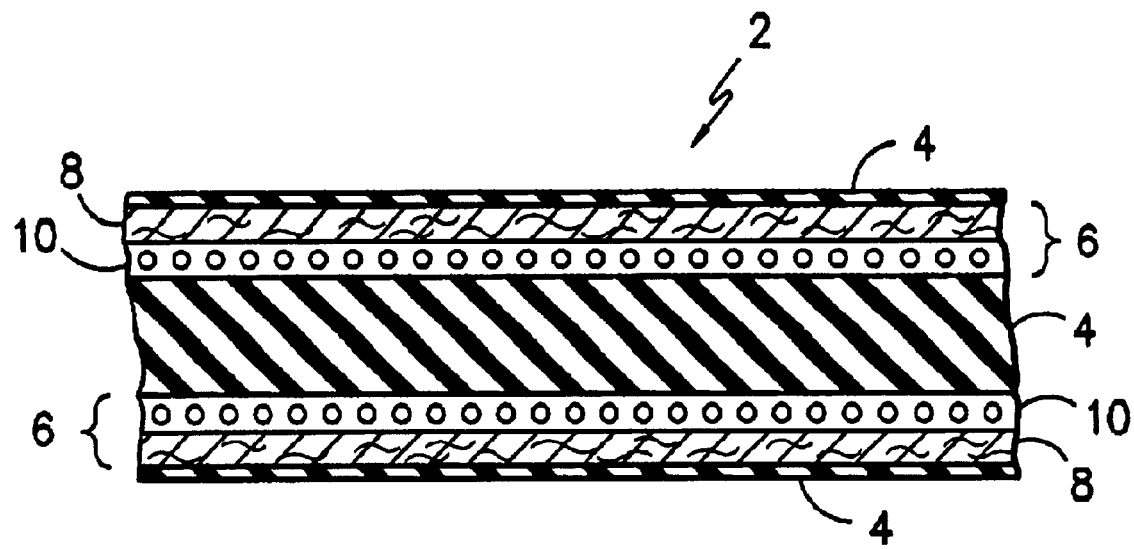
FIG. -1-
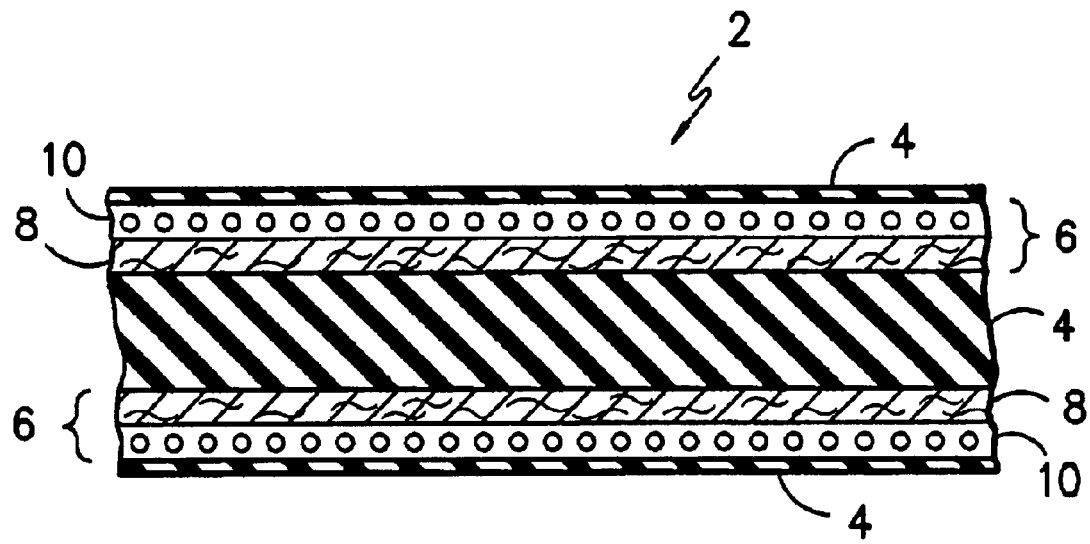
FIG. -2-

US 6,838,163 B2

COMPOSITE FACER FOR WALLBOARDS

BACKGROUND OF THE INVENTION

The present invention relates to facers for wallboards and methods for making wallboards containing such facers. More specifically, the present invention includes a composite facer for wallboards comprising a nonwoven mat that is adhesively bonded to a scrim fabric reinforcement.

Traditional wallboard contains a cementitious material, such as gypsum or plasterboard, and paper facing on one or both sides thereof. This type of wallboard has various disadvantages. First, the paper facing is generally flammable, which is not usually a desirable quality for wallboards used in building construction. Secondly, if the paper facing gets wet, it tends to peel away from the gypsum or plasterboard core and the structural integrity of the paper decreases, which ultimately allows degradation of the entire wallboard. Further, the paper facing does not impart much strength to the wallboard when wet.

Several attempts have been made to solve these problems. All patents mentioned are hereby incorporated herein by reference in their entirety. U.S. Pat. No. 4,378,405, issued to Pilgrim, discloses a gypsum board having a nonwoven glass fiber tissue embedded in the face of the core and a continuous film of the cementitious material having a higher density and lower porosity than the core extending over the outer face of the tissue. The method for making this product includes the step of vibrating the layer of slurry in contact with the tissue until the slurry penetrates the tissue until it is completely embedded, thus requiring extensive and expensive modification of existing wallboard manufacturing lines.

U.S. Pat. No. 4,810,569, issued to Lehnert et al., discloses a fibrous matfaced gypsum board in which the set gypsum core is sandwiched between two sheets of porous glass mat, with the outer surface of at least one of said mats being substantially free of set gypsum. A disadvantage to this arrangement is that the glass fiber mat is exposed on the outer face of the board, which is an irritant to the skin of workers and others who come into contact with the facing thereof.

International Application Number PCT/NZ98/00105, having International Publication Number WO 99/04112, discloses a reinforced plasterboard having a first layer of paper, a core of a cementitious material, a mesh reinforcement, and adjacent to that mesh reinforcement a further layer of paper. The disadvantages of wallboards having paper facing are outlined above.

Thus, it would be desirable to provide a composite facing material that could be used in place of paper and other facing products to provide a wallboard with superior strength, fire resistance, and water resistance at a reasonable cost. Further, it would be desirable to provide a facing material that may be easily adjusted to conform to various strength requirements. None of the prior art discloses a composite wallboard facing material made from a nonwoven polyester carded mat bonded to a reinforcing laid scrim layer made from continuous glass fibers, which allows a gypsum slurry to penetrate and embed the composite in a face of the wallboard.

OBJECTS OF THE INVENTION

Accordingly, it is an object of the present invention to provide a composite facing material for wallboard that improves strength, fire resistance, and water resistance of the wallboard.

Another object of the present invention is to provide a composite facing material for wallboard that may be substituted into an existing wallboard assembly line, without extensive and expensive modifications thereto.

Another object of the present invention is to provide a composite facing material that allows adjustment of the strength characteristics without having to vary the nonwoven mat component.

Yet another object of the present invention is to provide a wallboard that is reinforced and that does not contain exposed reinforcement fibers, such as glass fibers, on the face of the wallboard. Such an arrangement without exposed glass fibers on the exterior of the board prevents skin irritation for workers and others coming into contact with the face of the wallboard.

Still another object of the present invention is to provide a composite facing material for wallboards having superior adhesion to the cementitious core material, so that the composite fibers tend to break rather than pull out of the core material.

BRIEF DESCRIPTION OF THE DRAWINGS

These and other features, aspects, and advantages of the present invention will become better understood with regard to the following description, appended claims, and accompanying drawings where:

FIG. 1 is a cross-sectional view of a wallboard, showing composite material on a top and bottom face, where the composite material comprises a nonwoven mat bonded to a reinforcement scrim fabric layer, and wherein the nonwoven mat is oriented outwardly toward a face of the wallboard, while the reinforcement scrim fabric layer is facing inwardly toward a core of the wallboard; and FIG. 2 is a cross-sectional view of an alternate embodiment of a wallboard, showing the composite material on a top and bottom face, where the composite material comprises a nonwoven mat bonded to a reinforcement scrim fabric layer, and wherein the reinforcement scrim fabric layer is oriented outwardly toward a face of the wallboard, while the nonwoven mat is facing inwardly toward a core of the wallboard.

DETAILED DESCRIPTION

FIG. 1 shows a wallboard 2 having an integral matrix of cementitious material as a core 4, and a composite facer material 6 embedded in a top and bottom face thereof. The composite facer material, in a most preferred embodiment, comprises two layers. The first layer is preferably a carded polyester nonwoven mat 8, which is bonded to a laid scrim reinforcement layer 10 made of continuous glass fibers. The two layers are preferably bonded together using an acrylic adhesive, which offers superior adhesion between the layers as well as superior adhesion between the composite facing material and the cementitious core. It should be understood that other adhesives or polymeric binders may be used, including without limitation polyvinyl acetate adhesive, polyester, polyacrylates, polyvinylidene chlorides, polyvinyl alcohols, styrene budadiene rubber, or polyvinyl chloride. Other adhesive methods may be used as well, including without limitation heat bonding, or ultrasonic bonding. A suitable adhesive material or method will bond the yarns of the reinforcement fabric together, bond the yarns to the mat, and will bond the composite material to the core.

The composite facer should be constructed in such a manner that allows aqueous cementitious slurry, such as gypsum or plasterboard, to flow through the composite facer material, thus embedding the composite facer just below the surface of the face. Other suitable core materials include gypsum, concrete, mineral wool, rock wool, and any suitable combination thereof. A film of the cementitous material should be formed completely over the composite facer in the final wallboard construction. Because the face of the wallboard comprises the cementitious slurry, a waterproofing additive may be included therein. Any suitable waterproofing additive may be used, including, but not limited to, a wax emulsion, silicone, asphalt, or any hydrophobic latex or emulsion. Further, the outer facings of the wallboard may be coated with mildew resistant or weather resistant coatings. Weather resistant coatings may include ultraviolet protective coatings such as silicones or ultraviolet absorbers. Waterproofing coatings may include silicones, acrylic or other latex compounds, or film forming polymeric coatings, such as polyurethanes. Mildew resistant coatings may include antimicrobial or antifungal agents.

The nonwoven mat is preferably a carded polyester nonwoven mat, although other suitable materials may be used, including glass, basalt, olefin, or any other materials that meet the requirements set forth herein. Further, although the nonwoven mat is preferably carded, it may also be needlepunched, spunlaced, spunbonded, meltblown, airlaid, hydroentangled, or formed using any suitable combination thereof. The weight of the nonwoven mat will preferably be in the range of about 0.25 ounces per square yard to about 2.0 ounces per square yard. The most preferred weight range of the nonwoven mat is between about 0.5 ounces per square yard to about 1.5 ounces per square yard.

The reinforcing scrim fabric material should be strong enough to survive the rigors of board manufacture, and should be open enough to allow gypsum to flow through. In a preferred embodiment, the scrim fabric exhibits hydrophobic properties to obtain low moisture regain. Continuous glass fiber is the preferred material for the fabric reinforcement component, but it should be understood that other suitable materials might be used, including synthetic materials such as polyesters, polyamides, or polyolefins. Natural fibers may be used as well, including inorganics, such as basalt or another mineral fiber, as well as organic fibers such as carbon fibers and cellulosics such as cotton or rayon. The fabric should also be formed from a high modulus, low elongation yarn construction. The preferred scrim configuration is a tri-directional laid scrim, but other configurations such as woven scrim or knitted scrim would be suitable as well. The term "laid scrim," as used herein, generally means an adhesively bonded scrim fabric. The most preferred scrim is a matrix of machine direction glass yarns and cross-machine direction glass yarns. It should be understood that while the reinforcement layer has been described as a scrim fabric, any suitable fabric may be employed for this purpose, as long as it possesses the requisite properties outlined above.

The scrim fabric provides most of the strength of the composite. If a higher strength composite is required for a particular application, either the density of the scrim yarn or the denier (size) of the scrim yarn may be increased accordingly. This arrangement allows a variety of different scrim fabrics to be used with a single type of nonwoven mat. The scrim fabric yarn density, in a preferred embodiment, ranges between about 1 thread per inch and about 20 threads per inch. In a most preferred embodiment, the scrim fabric yarn density ranges between about 4 threads per inch and about 10 threads per inch. The preferred yarn size in the scrim fabric is between about 40–4000 denier. The more preferred range of yarn size in the scrim fabric is between about 150–2000 denier. The most preferred range of yarn size in the scrim fabric is between about 220–1300 denier.

Also, the flexibility of the composite material facilitates folding of the facing material around the edges of the wallboard, similarly to paper facings. It should be noted that the composite may also be positioned within the core so that the scrim portion is facing away from the core, as shown in FIG. 2. An advantage to this configuration is that it reduces the likelihood that the yarn will cut into or compress the core. Further, as a board is flexed, the yarn presses against the nonwoven mat and the load is then transferred to a lager area of the core, thus providing additional strength.

EXAMPLE I

A facer material was constructed from a laid scrim of G150 glass yarn in a tri-axial configuration laminated to a 0.5 ounce/square yard carded polyester mat bonded with an acrylic adhesive. The yarn frequency was 4 yarns per inch in each direction. The facer was laid into a silicone mold 3 inches by 11 inches and 0.5 inches deep. The mold was filled with gypsum slurry covering the facer. In one trial, the facer was placed with the scrim facing the gypsum (as shown in FIG. 1), in another, the mat was facing the gypsum (as shown in FIG. 2). The slurry was allowed to set for 20 minutes after which the composites were removed from the mold and cured at 40° C. for 24 hours.

The flexural break strength was measured according to ASTM C473. The break strength of the composite with the scrim facing the gypsum (FIG. 1) was 21.4 pounds. The break strength of the composite with the mat facing the gypsum (FIG. 2) was 29.4 pounds.

Thus, it can be seen that the orientation of the composite within the wallboard makes a significant difference in the flexural break strength thereof. When the scrim reinforcing fabric layer is facing outwardly, away from the core of the wallboard, the flexural strength is increased dramatically.

An alternate embodiment of the composite may be used, wherein a three layer composite is provided. In this embodiment, the scrim layer is sandwiched between two layers of a nonwoven mat. This arrangement also provides additional strength. The three layer embodiment provides the strength benefits of having the nonwoven mat facing toward the core, combined with the benefit of preventing the glass fibers of the reinforcing scrim fabric layer from protruding through the face of the wallboard.

Although the present invention has been described in considerable detail with reference to certain preferred versions thereof, other versions are possible. Therefore, the spirit and scope of the appended claims should not be limited to the description of the preferred versions contained herein.

What is claimed is:

1. A wallboard comprising:
   an integral matrix of set cementitious material extending from one face of the board to the other face of the board; and
   a composite material including a carded nonwoven mat and a reinforcing fabric layer bonded together, wherein said cementitious material extends over an outer face of said composite material.

2. The wallboard set forth in claim 1, wherein said carded nonwoven mat is made of material selected from the group consisting of polyester, mineral fiber, polyolefin, glass, basalt, polyamides, and any combination thereof.

3. The wallboard set forth in claim 2, wherein said carded nonwoven mat is polyester.

4. The wallboard set forth in claim 1, wherein said reinforcing fabric layer is made of material selected from the group consisting of glass, mineral fiber, basalt, polyester, polyolefin, polyamides, and any combination thereof.

5. The wallboard set forth in claim 4, wherein said glass fabric layer includes continuous glass yarns.

6. The wallboard set forth in claim 1, wherein said mat and said fabric layer are bonded together by an adhesive layer positioned between said mat and said fabric layer, said adhesive being selected from the group consisting of polyacrylates, polyvinyl acetate, polyvinyl alcohol, polyvinyl chloride, polyolefin, styrene butadiene rubber, acrylic adhesive, polyvinylidene chloride, and any combination thereof.

7. The wallboard set forth in claim 1, wherein said mat and said fabric layer are heat bonded together.

8. The wallboard set forth in claim 1, wherein said mat and said fabric layer are ultrasonically bonded together.

9. The wallboard set forth in claim 1, further comprising a second layer of said composite material wherein said second layer of composite material is embedded in an opposite face from said first layer of composite material, and wherein a continuous film of said cementitious material extends over an outer face of said second layer of composite material.

10. The wallboard set forth in claim 1, wherein said fabric layer is selected from the group consisting of woven fabric, knitted fabric, and adhesively bonded fabric.

11. The wallboard set forth in claim 1, wherein said reinforcing fabric layer has a yarn density of between 1 thread per inch and 20 threads per inch.

12. The wallboard set forth in claim 11, wherein said reinforcing fabric layer has a yarn density of between 4 threads per inch and 10 threads per inch.

13. The wallboard set forth in claim 1, wherein yarn size in said reinforcing fabric layer is in the range between 40 and 4000 denier.

14. The wallboard set forth in claim 13, wherein said yarn size in said reinforcing fabric layer is in the range between 150 and 2000 denier.

15. The wallboard set forth in claim 14, wherein said yarn size in said reinforcing fabric layer is in the range between 220 and 1300 denier.

16. The wallboard set forth in claim 1, wherein said composite is oriented in said wallboard so that said nonwoven mat is facing an outer face of said wallboard, and said reinforcing fabric layer is facing inwardly toward a core of said cementitious material.

17. A method for manufacturing wallboard, said method comprising the steps of:
    bonding a carded nonwoven mat to a reinforcing fabric layer to form a composite material;
    providing an aqueous cementitious slurry, and bringing said composite material into contact with said slurry; and
    allowing said cementitious slurry to flow through and penetrate said composite material to form a continuous film extending over an outer face of said composite material.

18. The method set forth in claim 17, further comprising the step of providing a second layer of composite material, and embedding said second layer of composite material on an opposite side of said cementitious slurry from said first layer of composite material.

19. The method set forth in claim 17, wherein said carded nonwoven mat is made of material selected from the group consisting of polyester, mineral fiber, polyolefin, glass, basalt, polyamides, and any combination thereof.

20. The method set forth in claim 19, wherein said carded nonwoven mat is polyester.

21. The method set forth in claim 17, wherein said reinforcing fabric layer is made of material selected from the group consisting of glass, mineral fiber, basalt, polyester, polyolefin, polyamides, and any combination thereof.

22. The method set forth in claim 21, wherein said glass fabric includes continuous glass yarns.

23. The method set forth in claim 17, wherein said mat and said fabric are bonded together by an adhesive layer positioned between said mat and said fabric layer, said adhesive being selected from the group consisting of polyacrylates, polyvinyl acetate, polyvinyl alcohol, polyvinyl chloride, polyolefin, styrene butadiene rubber, acrylic adhesive, polyvinylidene chloride, and any combination thereof.

24. The method set forth in claim 17, wherein said mat and said fabric are heat bonded together.

25. The method set forth in claim 17, wherein said mat and said fabric are ultrasonically bonded together.

26. The method set forth in claim 17, wherein said cementitious material is selected from the group consisting of gypsum, concrete, mineral fibers, and any combination thereof.

27. The method set forth in claim 17, wherein said fabric is selected from the group consisting of woven fabric, knitted fabric, and adhesively bonded fabric.

28. The method set forth in claim 17, wherein said reinforcing fabric layer has a yarn density of between 1 thread per inch and 20 threads per inch.

29. The method set forth in claim 28, wherein said reinforcing fabric layer has a yarn density of between 4 threads per inch and 10 threads per inch.

30. The method set forth in claim 17, wherein yarn size in said reinforcing fabric is in the range between 40 and 4000 denier.

31. The method set forth in claim 30, wherein said yarn size in said reinforcing fabric is in the range between 150 and 2000 denier.

32. The method set forth in claim 31, wherein said yarn size in said reinforcing fabric is in the range between 220 and 1300 denier.

33. The method set forth in claim 17, further including the step of orienting the composite material so that said nonwoven mat is facing an outer face of said wallboard, and said reinforcing fabric layer is facing inwardly toward a core of said set cementitious material.

34. A paperless wallboard comprising:
    an integral matrix of set cementitious material extending from one face of the board to the other taco of the board; and
    a composite material including a carded nonwoven mat and a reinforcing fabric layer bonded together, wherein said cementitious material extends over an outer face of said composite material.

* * * * *

UNITED STATES PATENT AND TRADEMARK OFFICE
CERTIFICATE OF CORRECTION

PATENT NO.    : 6,838,163 B2
DATED         : January 4, 2005
INVENTOR(S)   : Robert M. Smith et al.

Page 1 of 1

It is certified that error appears in the above-identified patent and that said Letters Patent is hereby corrected as shown below:

Column 6,
Line 56, delete the word "taco" and insert the word -- face --.

Signed and Sealed this

Twenty-sixth Day of April, 2005

JON W. DUDAS
*Director of the United States Patent and Trademark Office*